(12) United States Patent
    Paradis

(10) Patent No.: US 11,376,183 B2
(45) Date of Patent:       Jul. 5, 2022

(54) DEVICE FOR TREATING A PART OF THE HUMAN BODY COMPRISING AT LEAST ONE MAGNETISED NEEDLE

(71) Applicant: Line Paradis, Dubai (AE)

(72) Inventor: Line Paradis, Dubai (AE)

( * ) Notice: Subject to any disclaimer, the term of this patent is extended or adjusted under 35 U.S.C. 154(b) by 0 days.

(21) Appl. No.: 16/957,501

(22) PCT Filed: Oct. 19, 2018

(86) PCT No.: PCT/FR2018/052608
    § 371 (c)(1),
    (2) Date: Jun. 24, 2020

(87) PCT Pub. No.: WO2019/207212
    PCT Pub. Date: Oct. 31, 2019

(65) Prior Publication Data
    US 2021/0031049 A1       Feb. 4, 2021

Related U.S. Application Data

(63) Continuation of application No. PCT/FR2018/051058, filed on Apr. 26, 2018.

(30) Foreign Application Priority Data

Apr. 26, 2018   (FR) .................. PCT/FR2018/051058

(51) Int. Cl.
    *A61N 2/00*        (2006.01)
    *A61H 7/00*        (2006.01)
    (Continued)

(52) U.S. Cl.
    CPC ........... *A61H 7/001* (2013.01); *A61M 35/003* (2013.01); *A61M 37/0076* (2013.01);
    (Continued)

(58) Field of Classification Search
    CPC ....... A61H 39/086; A61H 39/00; A61H 39/08
    See application file for complete search history.

(56) References Cited

U.S. PATENT DOCUMENTS 4,508,119 A * 4/1985 Tukamoto ............ A43B 1/0054
                                                    128/907
5,968,063 A * 10/1999 Chu ....................... A61H 39/08
                                                    604/117
(Continued)

FOREIGN PATENT DOCUMENTS

CN      101232858 A      7/2008
DE    102011120366 A1    6/2013
(Continued)

OTHER PUBLICATIONS

International Search Report and Written Opinion from PCT Application No. PCT/FR2018/052608, dated Feb. 5, 2019.

*Primary Examiner* — Samuel G Gilbert
(74) *Attorney, Agent, or Firm* — Workman Nydegger

(57) ABSTRACT

A cosmetic treatment method and device for treating a part of the human body. The device includes a treatment portion including at least one magnetised needle intended to come into contact with a part of the human body and a motorised drive device connected to the treatment portion and capable of imposing movement upon the at least one magnetised needle. The movement is a translational movement and the treatment portion includes a single magnetised needle or a plurality of magnetised needles secured together by welding.

10 Claims, 2 Drawing Sheets

(51) Int. Cl.
*A61M 35/00* (2006.01)
*A61M 37/00* (2006.01)
*A61N 2/12* (2006.01)

(52) U.S. Cl.
CPC ............... *A61N 2/004* (2013.01); *A61N 2/12* (2013.01); *A61H 2201/123* (2013.01)

(56) References Cited

U.S. PATENT DOCUMENTS

| | | | |
|---|---|---|---|
| 8,226,540 B1 * | 7/2012 | Chi | A61H 39/086 600/9 |
| 9,005,158 B2 | 4/2015 | Danenberg et al. | |
| 2005/0061198 A1 * | 3/2005 | Khan | C09D 11/02 106/31.03 |
| 2008/0177286 A1 | 7/2008 | Khan et al. | |
| 2008/0221548 A1 | 9/2008 | Danenberg et al. | |
| 2011/0295067 A1 * | 12/2011 | Rodriguez Fernandez | A61B 17/3423 600/114 |
| 2017/0035461 A1 * | 2/2017 | Deal | A61B 17/52 |

FOREIGN PATENT DOCUMENTS

| | | | |
|---|---|---|---|
| GB | 2474671 A | 4/2011 | |
| KR | 20130058843 A | 6/2013 | |
| RU | 164483 U1 | 9/2016 | |
| WO | 2005110395 A1 | 11/2005 | |
| WO | 2007011788 A2 | 1/2007 | |
| WO | 2017210017 A1 | 12/2017 | |

* cited by examiner

DEVICE FOR TREATING A PART OF THE HUMAN BODY COMPRISING AT LEAST ONE MAGNETISED NEEDLE

BACKGROUND OF THE INVENTION

Different techniques are currently available to remove pigment marking on skin or lips.

Pigment marking can be composed of tattoo pigments and different tattooing methods have been developed. Among existing tattoo removal techniques, mention can be made of methods using a tattoo removal composition which dissolves tattoo pigments and causes expelling thereof onto the surface of the skin. These techniques afford good results but further perfection thereof can be desirable by reducing the number of sessions required for complete tattoo removal.

Tattooing is an event which intentionally leads to the formation of pigment marking. However, there may exist other events, which are non-intentional, leading to modification of the appearance of part of the body and the onset of pigment marking. This is particularly the case when the subject has been exposed to the blast of an explosive device which led to the embedding of metal fragments in the subject's skin. This is also the case when the subject has suffered a road accident which may result in the embedding of asphalt or tar particles.

It is known to use a laser radiation technique to remove said pigment marking. However, this technique is not fully satisfactory since it does not always lead to complete removal. In some cases, this technique even leads to additional cosmetically unpleasing impairment of the appearance of the treated surface.

The Applicant has searched methods for efficient removal of pigment marking of the skin and lips without any noteworthy impairment of the appearance of the treated surface.

SUBJECT AND SUMMARY OF THE INVENTION

According to a first embodiment, the invention proposes a motorised device for treating a part of the human body, comprising at least:
a treatment portion comprising at least one magnetised needle intended to come into contact with a part of the human body; and
a motorised drive device connected to the treatment portion and capable of imposing movement upon said at least one magnetised needle, and when this movement is a translational movement the treatment portion comprises a single magnetised needle or a plurality of magnetised needles secured together by welding.

According to a second embodiment, the invention proposes a non-motorised device for treating a part of the human body, in the form of a handpiece comprising at least:
a treatment portion comprising at least one magnetised needle intended to come into contact with a part of the human body; and
a grip portion.

The above-described first and second embodiments use at least one magnetised needle to perform treatment of a part of the human body. The part of the human body can be the skin or lips. To the Applicant's knowledge, it is not known to use a magnetised needle for the treatment of a part of the human body. In the first embodiment, a motor sets said at least one magnetised needle in movement, whereas the movement thereof is solely produced by the handling of an operator in the second embodiment. In the second embodiment, the device is devoid of a motor and drive device.

The device according to the invention advantageously allows efficient removal of pigment marking on the skin or lips without impairing the appearance of the treated surface in noteworthy manner. In particular, the Applicant has found that the devices described above can be used to extract an embedded metal compound through use of the magnetic attraction effect of this compound by said at least one magnetised needle. Therefore, these devices can be particularly useful for tattoo removal or for the extraction of fragments of metal compounds. In addition, research by the Applicant has evidenced other advantageous uses of these devices which shall be mentioned below. The removal of pigment marking on the skin or lips is therefore only one particular, nonlimiting use of the above-described devices.

In one example of embodiment, said at least one magnetised needle is formed of a material selected from among: stainless steel, titanium, titanium alloys or titanium nitride.

In one example of embodiment, the diameter of said at least one magnetised needle can be less than or equal to 0.40 mm, for example between 0.10 mm and 0.40 mm.

Different types of movements can be imparted to the magnetised needle(s) when the device is in use.

In particular, the device can be motorised and the drive device can be capable of imposing a translational movement upon said at least one magnetised needle. In particular, the drive device can be capable of imposing a back-and-forth movement upon said at least one magnetised needle.

According to another example, the treatment portion is in the form of a roller mobile in rotation about its axis and carrying said at least one magnetised needle. In this case, the device can be motorised or non-motorised.

In one example of embodiment, the treatment portion comprises a single magnetised needle. In this case also, the device can be motorised or non-motorised.

There is also described a motorised or non-motorised device for treating a part of a human body, comprising at least:
a treatment portion comprising one or more magnetised needles intended to come into contact with a part of the human body; and
a grip portion. The different characteristics described in the present disclosure apply to this object.

In one example of embodiment, said at least one magnetised needle has a magnetic induction field higher than 100 Gauss, for example between 100 Gauss and 6000 Gauss.

According to another aspect, the invention related to a cosmetic treatment method of the skin or lips using a device such as described above, comprising at least:
contacting said at least one magnetised needle with the skin or lips.

In one example of embodiment, a metal compound embedded in the skin or lips is extracted through use of the magnetic attraction of this compound by said at least one magnetised needle.

In particular, the method can be a tattoo removal method on the skin or lips, and the compound can be a tattoo pigment.

In a variant, the compound can be a compound accidentally embedded in the skin or lips. In this case, the compound is a metal fragment for example derived from an explosive device, or a fragment of tar or asphalt.

In another aspect, the invention relates to a method for manufacturing a device such as described above, comprising at least:

magnetising said at least one needle via subjection to a magnetic induction field of a permanent magnet having an intensity higher than or equal to 100 Gauss.

BRIEF DESCRIPTION OF THE DRAWINGS

Other characteristics and advantages of the invention will become apparent from the following description of particular embodiments of the invention given as nonlimiting examples, with reference to the appended drawings in which.

DETAILED DESCRIPTION OF EMBODIMENTS

Figure 1:
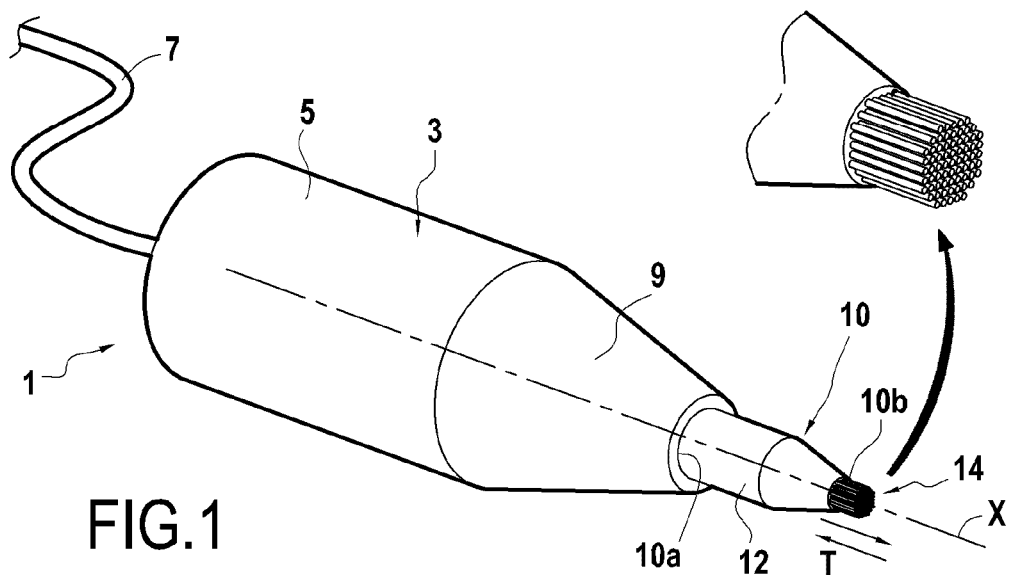
FIG. 1 schematically and partially illustrates an example of device according to the first embodiment of the invention (motorised device)

FIG. 1 illustrates an example of device 1 according to the invention. The device 1 is in the form of a handpiece. The device 1 comprises a body 3 having a proximal portion 5 in which there is housed a translational drive device. The drive device is configured to impose a back-and-forth translational movement upon a set of needles 14. The drive device forms a motorised device that is not original per se. The drive device is connected to an electricity generator (not illustrated) via an electric cable 7. The body 3 further has a distal portion 9 forming the grip portion. As an example of a body 3 enclosing a drive device that can be used in the invention, mention can be made of the commercial device "Dermo Power Pen" (Linda Paradis).

The device 1 further comprises an end-portion 10 connected to the body 3. This end-portion 10 comprises a casing 12 surrounding the set of needles 14. The set of needles 14 extends inside the casing 12. The needles forming the set of needles 14 are secured together and are held in a predetermined position. Here, the needles 14 are welded together. The needles 14 can be welded with or without the use of a filler material. The set 14 extends along a longitudinal axis X. The assembly formed by the casing 12 and the set of needles 14 is here in the form of a cartridge connected to the body 3. The casing 12 therefore defines a securing portion 10a of the end-portion 10 which is inserted in a housing arranged in the distal portion 9 of the body 3 to secure the end-portion 10 to the body 3.

The set of needles 14 forms the treatment portion of the device 1. The needles 14 are therefore intended to be placed in contact with the skin or lips to perform treatment. The distal portion 10b of the end-portion 10 is defined by the set of needles 14. The set of needles 14 projects from the casing 12.

The needles 14 are evidently sterile before using the device 1. The needles 14 are disposable needles. The needles 14 are magnetised. To magnetise the needles, a permanent magnet can be used having a magnetic induction field higher than 100 Gauss, for example between 100 Gauss and 6000 Gauss. The needles 14 can have a magnetic induction field higher than 100 Gauss, for example between 100 Gauss and 6000 Gauss.

The present invention is not limited to the use of a particular number of needles 14 in the device. Advantageously, and to reduce any risk of perforating the treated surface, a set of 88 or 132 needles can be used as described in application PCT/FR2018/051058 the content of which is incorporated herein by reference. However, it would remain within the scope of the invention if the set of needles comprised a different number of needles, in particular fewer than 88 needles or more than 132 needles. It is even possible to use a device having a single needle, as will be recalled below.

The needles 14 can be formed of a metal material e.g. stainless steel, titanium, a titanium alloy e.g. a titanium and gold alloy. For example, it is possible to use needles 14 in stainless steel having a weight content of nickel less than or equal to 9%, for example between 3% and 9%. Stainless steel can be of series 200 or 400.

Figure 2:
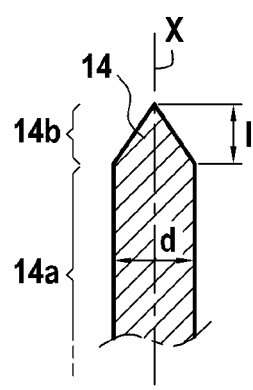
FIG. 2 schematically illustrates a detail of the device in FIG. 1.

The diameter d of each of the needles 14 can be greater than or equal to 0.10 mm. For example, this diameter d can be between 0.25 mm and 0.40 mm, and for example substantially equal to 0.3 mm or 0.35 mm. By "diameter", unless otherwise specified, it is meant the largest transverse dimension measure perpendicular to the longitudinal axis X. As illustrated in FIG. 2, the needles 14 may comprise a portion of constant diameter 14a extended by a tapered portion 14b of decreasing diameter. The tapered portion 14b defines the tip of the needle, this portion 14b being intended to come into contact with the surface to be treated. It is possible to use needles 14 having a short tip (needles known per se commonly called "short-taper needles"). Said needles 14 have a tip 14b having a length l shorter than or equal to 2 mm. However, it would remain within the scope of the invention if short-taper needles were not used. For example, the length of the magnetised needles 14, measured from one end of the needle to the other, can be longer than or equal to 1 cm, for example longer than or equal to 5 cm. However, it would remain within the scope of the invention if use is made of magnetised needles of shorter length are used.

When the drive device is actuated, the needles 14 are driven by a back-and-forth movement along axis X. This back-and-forth movement is denoted by the double arrow T in FIG. 1. This back-and-forth movement forms an alternating translational movement forwards and backwards along the axis X. When the drive device is actuated, the set of needles 14 is moved in a block with back-and-forth movement along the axis X.

One example of cosmetic treatment according to the invention using the device in FIG. 1 will now be described in connection with FIG. 3.

Figure 3:
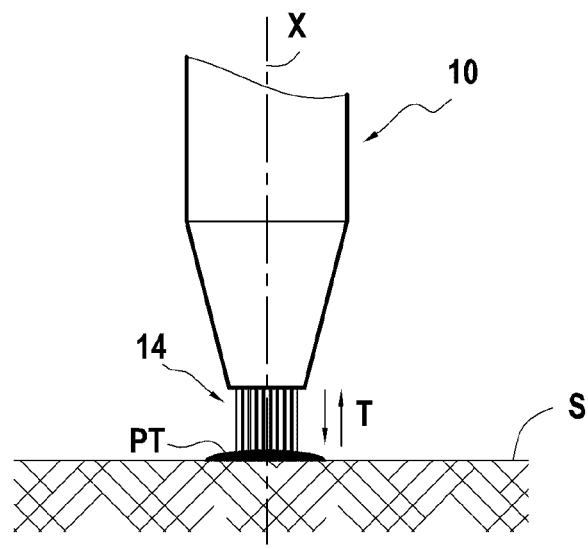
FIG. 3 schematically and partially illustrates an example of a cosmetic treatment method of the invention using the device in FIG. 1.

FIG. 3 illustrates the performing of cosmetic treatment of a surface S of the skin or lips. In particular, the surface S can be an area of the face or body. In the particular case illustrated in FIG. 3, the device 1 is an applicator of cosmetic product PT. However, the device 1 is not necessarily intended to apply a product and can be used alone as detailed below.

Initially, a cosmetic treatment product PT is applied to the set of needles 14. This product PT can be in the liquid state. Product PT can be configured to migrate through the surface S. The alternating pressure produced by the back-and-forth movement of the set of needles 14 contributes towards facilitating this migration. Product PT can allow performing of the cosmetic treatment at the dermis. In the example illustrated in FIG. 3, the device 1 is used to obtain removal of tattooing from the skin or lips. Product PT is a liquid tattoo removal composition able to migrate through the surface S. Said liquid composition allows extraction of tattoo ink towards outside of surface S to achieve tattoo removal. As an example of tattoo removal composition that can be used, mention can be made of the commercial composition "Tattoo Remoov"™ (Linda Paradis).

To perform application, the needles 14 impregnated with product PT are driven by a back-and-forth movement along axis X. The set 14 is moved transversally relative to the treated surface during application. The set of needles 14 has a piston effect which facilitates penetration of the product. The back-and-forth movement of the needles 14 causes detachment of the surface layer of the epidermis, the "stratum corneum", and causes a slight rise in temperature of the treated surface. This slight rise causes slight evaporation of water contained in the skin or lips, enabling product PT to be suctioned inside the skin or lips, since the product PT "Tattoo Remoov"™ comprises from 35% to 40% of water. Interaction of product PT with the tattoo pigment leads to the expelling of the latter outside the treated surface.

The use of magnetised needles 14 advantageously provides for faster and more efficient extraction of tattoo pigments from the skin or lips. These pigments are metal compounds that are attracted by the needles 14 via magnetic interaction, which facilitates extraction thereof and hence the efficacy of tattoo removal. In this example, magnetic interaction adds to the physicochemical effect produced by the use of the applicator and tattoo removal product PT to optimise the efficacy of the tattoo removal operation. The implementation of this method advantageously provides a particularly efficient tattoo removal technique necessitating a reduced number of sessions to achieve complete removal of tattoo pigment marking.

In connection with FIGS. 1 to 3, an example has been described for a device according to the first embodiment (with motorised device). However, the device of the invention is not limited to said structure as is illustrated below.

Figure 4:
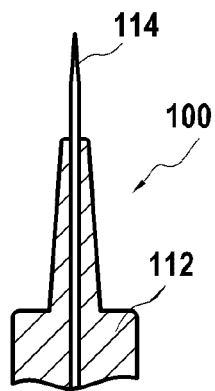
FIG. 4 schematically and partially illustrates a variant of device according to the first embodiment of the invention.
Figure 5:
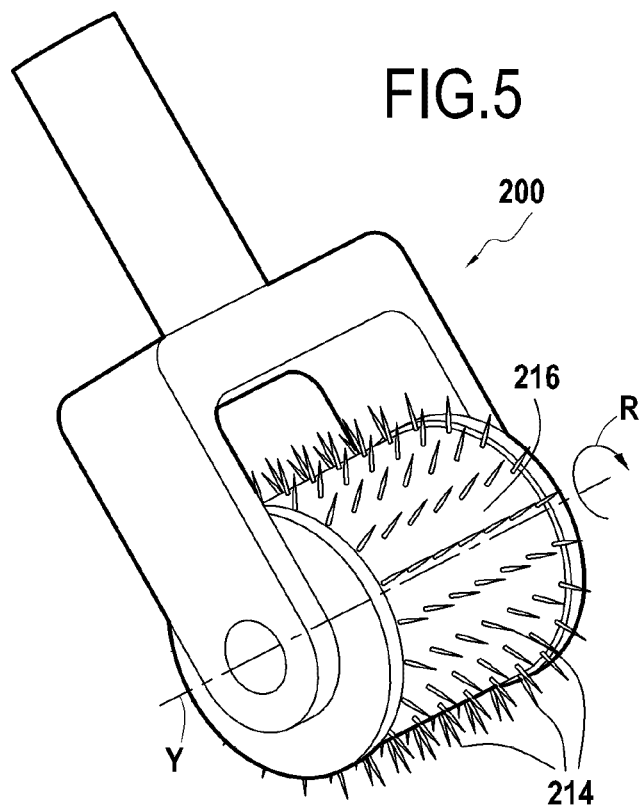
FIG. 5 schematically and partially illustrates another variant of device according to the first embodiment of the invention.

FIG. 4 illustrates a variant of the motorised device 100 which this time comprises a single magnetised needle 114 contained in a casing 112 and mobile in translation. FIG. 5 illustrates another variant of this motorised device 200 which comprises a treatment portion in the form of a roller 216 mobile in rotation about its axis Y and carrying a plurality of magnetised needles 214. The motor is intended to set the roller 216 and needles 214 in rotation about axis Y of the roller. This rotation is represented by arrow R in FIG. 5. The roller device 200 in FIG. 5 can be in the form of a handpiece. However, it would remain within the scope of the invention if the device is provided with said structure for the treatment portion but does not have a motor.

Figure 6:
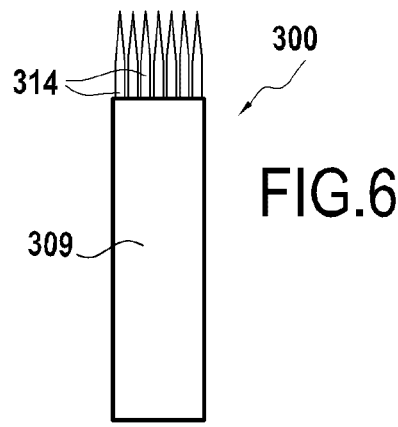
FIG. 6 schematically and partially illustrates an example of device according to the second embodiment of the invention (non-motorised device)
Figure 7:
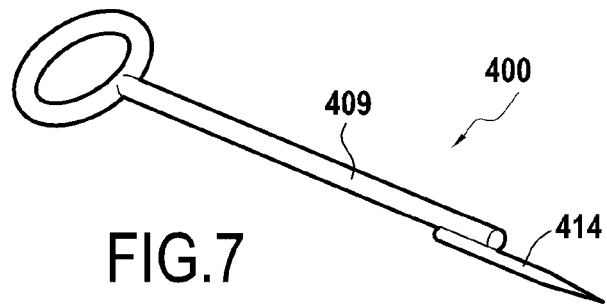
FIG. 7 schematically and partially illustrates a variant of device according to the second embodiment of the invention.

FIGS. 6 and 7 illustrate examples of devices according to the second embodiment (non-motorised device). The example of device 300 in FIG. 6 comprises a plurality of magnetised needles 314 assembled at one same grip portion 309. The example of device 400 in FIG. 7 comprises a single magnetised needle 414 connected to a grip portion 409. The grip portion 309 or 409, as illustrated, can be separate from the treatment portion comprising the magnetised needle(s) 314 or 414. As a variant, a first portion of the magnetised needle can form the treatment portion and a second portion of this needle can form the grip portion.

In connection with FIG. 3 a skin or lip tattoo removal method has been described, but the devices with magnetised needle(s) according to the invention are of particular advantage for other uses.

In particular, the devices can be used to extract fragments comprising a metal compound that have been accidently embedded, such as fragments from an explosive device or fragments of tar or asphalt (in the event of a road accident). According to these examples, the magnetising of the needle (s) allows extraction of fragments via magnetic interaction in a manner that is efficient and without any noteworthy impairment of the appearance of the treated surface which can be a result of laser treatment. Through the mention of these examples it will be noted in particular that the devices are not necessarily intended to apply a product to the skin or lips.

For the uses just described, a metal compound embedded in the skin or lips is extracted through use of the magnetic attraction of this compound by said at least one magnetised needle. However, the devices are not limited to said uses.

Said at least one magnetised needle can also be used alone or with a treatment product to improve the appearance of the skin insofar as the application of a magnetic field has a beneficial effect on skin appearance, in particular face skin. Advantage can also be taken of the magnetic effect produced by said at least one magnetised needle for medical purposes. In this case, the magnetic field generated by said at least one magnetised needle can be used to fluidise blood in particular to eliminate a blood clot. The device can therefore find application in the treatment of an inner part of the body and not only for the treatment of the skin or lips.

The expression "between . . . and . . . " is to be construed as including the limits.

The invention claimed is:

1. A cosmetic treatment method of skin or lips using a motorised device for treating a part of a human body, said motorised device including at least a treatment portion comprising at least one magnetised needle intended to come into contact with the part of the human body, said at least one magnetised needle having a magnetic induction field higher than 100 Gauss, and a motorised drive device connected to the treatment portion and capable of imposing movement upon said at least one magnetised needle, the cosmetic treatment method comprising:
    contacting said at least one magnetised needle with the skin or lips; and
    extracting a metal compound embedded in the skin or lips through use of the magnetic attraction of the metal compound with said at least one magnetised needle,
wherein the cosmetic treatment method is a pigment removal method on the skin or lips, wherein the metal compound is a pigment.

2. The cosmetic treatment method according to claim 1, wherein said at least one magnetised needle is formed of a material selected from among: stainless steel, titanium, titanium alloys or titanium nitride.

3. The cosmetic treatment method according to claim 1, wherein the drive device imposes a translational movement upon said at least one magnetised needle.

4. The cosmetic treatment method according to claim 1, wherein the treatment portion comprises a single magnetised needle.

5. The cosmetic treatment method according to claim 1, wherein the cosmetic treatment method is a tattoo pigment removal method on the skin or lips, wherein the metal compound is a tattoo pigment.

6. The cosmetic treatment method according to claim 1, wherein said treatment portion is in the form of a roller that is mobile in rotation about a longitudinal axis of the roller and carries said at least one magnetised needle.

7. A cosmetic treatment method of skin or lips using a non-motorised device for treating a part of a human body, in the form of a handpiece, said non-motorized device including at least a treatment portion comprising at least one magnetised needle intended to come into contact with the part of the human body, said at least one magnetised needle having a magnetic induction field higher than 100 Gauss, and a grip portion, said cosmetic treatment method comprising:

contacting said at least one magnetised needle with the skin or lips; and extracting a metal compound embedded in the skin or lips through use of magnetic attraction of the metal compound with said at least one magnetised needle, wherein the cosmetic treatment method is a pigment removal method on the skin or lips, wherein the metal compound is a pigment, and wherein said treatment portion is in the form of a roller that is mobile in rotation about a longitudinal axis of the roller and carries said at least one magnetised needle.

8. The cosmetic treatment method according to claim 7, wherein said at least one magnetised needle is formed of a material selected from among: stainless steel, titanium, titanium alloys or titanium nitride.

9. The cosmetic treatment method according to claim 7, wherein the cosmetic treatment method is a tattoo removal method on the skin or lips and wherein the metal compound is a tattoo pigment.

10. A motorised device for treating a part of a human body, the motorised device comprising:

a treatment portion comprising at least one magnetised needle intended to come into contact with the part of the human body;

said at least one magnetised needle having a magnetic induction field higher than 100 Gauss; and a motorised drive device connected to the treatment portion and capable of imposing movement upon said at least one magnetised needle, wherein said treatment portion is in the form of a roller that is mobile in rotation about a longitudinal axis of the roller and carries said at least one magnetised needle.

\* \* \* \* \*